(12) United States Patent
Ross

(10) Patent No.: US 6,322,986 B1
(45) Date of Patent: Nov. 27, 2001

(54) METHOD FOR COLORECTAL CANCER PROGNOSIS AND TREATMENT SELECTION

(75) Inventor: Jeffrey S. Ross, New Lebanon, NY (US)

(73) Assignee: Albany Medical College, Albany, NY (US)

( * ) Notice: Subject to any disclaimer, the term of this patent is extended or adjusted under 35 U.S.C. 154(b) by 0 days.

(21) Appl. No.: 09/484,554

(22) Filed: Jan. 18, 2000

(51) Int. Cl.⁷ .................... C12Q 1/68; A61K 39/395; A61K 48/00; C12P 19/34
(52) U.S. Cl. .................... 435/6; 424/85.1; 435/91.2; 514/44
(58) Field of Search ........... 435/6, 91.2; 424/85.1; 514/44

(56) References Cited

PUBLICATIONS

Hayner–Buchan et al, "HER–2/neu oncogene amplification determined by FISH is an independent predictor of survival in colorectal adenocarcinoma", Lab. Invest. 79(1) 76 A, Jan. 1999.*

Ross et al, "Prognostic significance of HER–2/neu gene amplification status by FISH prostate carcinoma", Cancer 79(11):2162–2170, Jun. 1997.*

Wisecarver et al, "HER–2/neu testing comes of age", Am. J. Clin. Pathol. 111:299–301, Mar. 1999.*

Fernandez–trigo et al, "Prognostic implications of chemoresistance–sensitivity assays for colorectal and appendiceal cancer", Am. J. Clin. Oncol. 18(5):454–60 Abstract Only, Oct. 1995.*

Scheithauer et al, "Treatment of patients with advanced colorectal cancer with cisplatin, 5–fluorouracil and leucovorin", Cancer 67:1294–1298, Mar. 1991.*

Pietras et al, "Remission of human breast cancer xenografts on therapy with humanized monoclonal antibody to HER–2 receptor and DNA reactive drugs", Oncogene 17:2235–2249, Jan. 1999.*

\* cited by examiner

Primary Examiner—Jeffrey Fredman
(74) Attorney, Agent, or Firm—Heslin Rothenberg Farley & Mesiti P.C.

(57) ABSTRACT

A method predicting the outcome, and prognosis and indicating treatment for patients afflicted with colorectal cancer by determining whether the number of copies of HER-2/neu gene in cancer cells from the patient exceeds four by in-situ hybridization. Patients having cells with five or more copies of the HER-2/neu gene are to be treated more aggressively or in combination with an anti-HER-2/neu antibody.

8 Claims, 1 Drawing Sheet

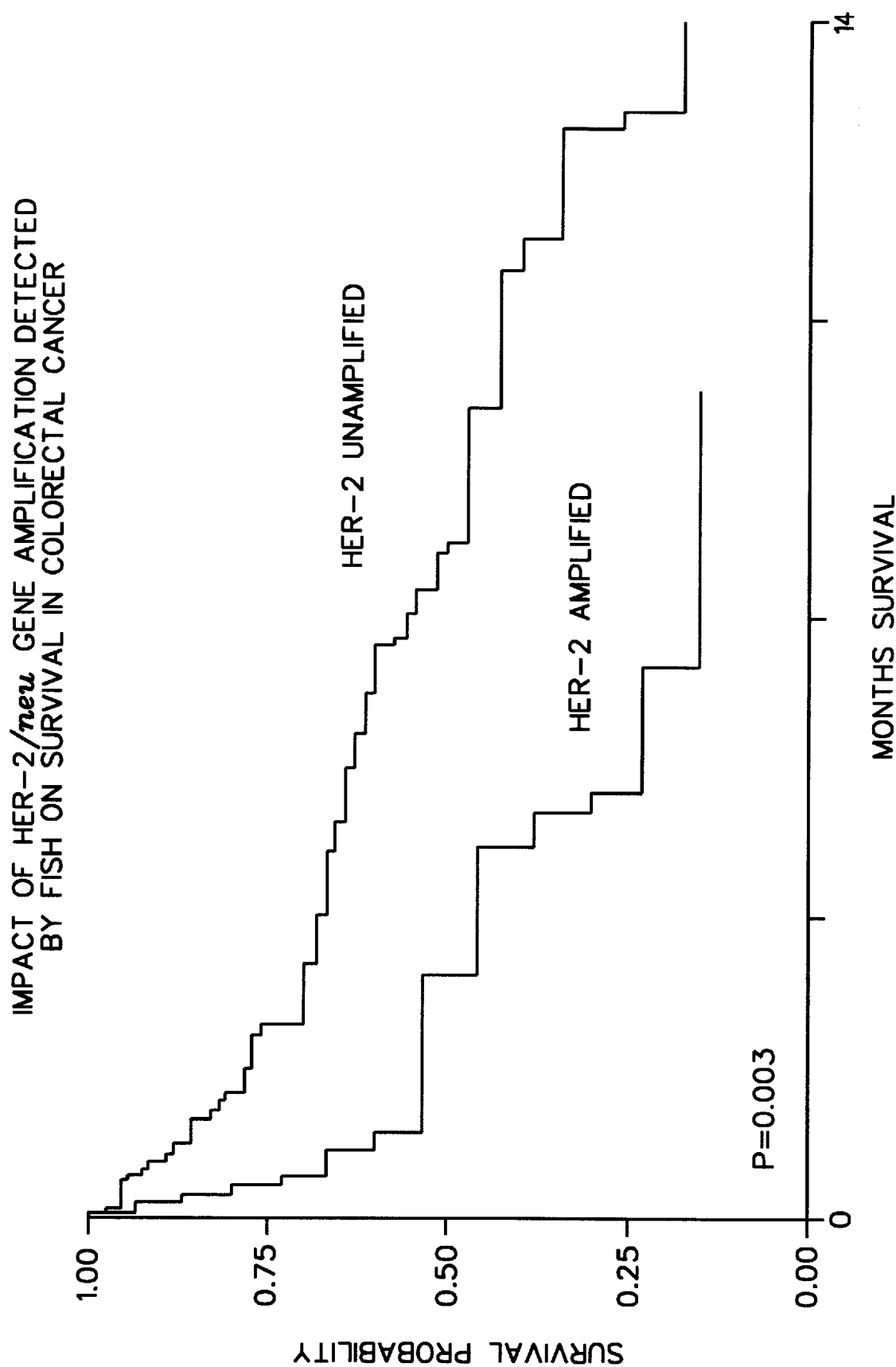

METHOD FOR COLORECTAL CANCER PROGNOSIS AND TREATMENT SELECTION

This application is related to U.S. Ser. No. 09/152,934 filed Sep. 14, 1998, which is a continuation-in-part of U.S. Ser. No. 09/088,417, filed Jun. 1, 1998, which is a continuation-in-part of U.S. Ser. No. 08/832,745, filed Apr. 4, 1997, the contents of which are hereby incorporated by reference in their entirety into the subject application.

FIELD OF THE INVENTION

The present invention relates to predicting the outcome and selecting preferred treatments for colorectal cancer by DNA analysis.

BACKGROUND OF THE INVENTION

Colorectal cancer is a common cancer in the developed world and is a major cause of cancer death. The disease is diagnosed in about 129,400 people and is responsible for nearly 56,600 deaths per year in the United States alone. Traditional therapies for colorectal cancer include surgery, radiation therapy, and chemotherapy, with 5-fluorouracil, levamisole, leucovorin or semustine (methyl CCNU) being the preferred chemotherapeutic agents for colorectal adenocarcinoma.

After surgery or other treatment the ability to predict recurrence and to treat the patient appropriately becomes problematic. Post-surgical treatments have numerous undesired side effects which one wishes to avoid if possible. Conversely, failure to adequately treat any residual tumor cells may result in recurrence of the cancer. Pathological stage, clinical stage, patient age, various protein markers and cell proliferation index are each indicative of the aggressiveness of the cancer and prognostic of eventual outcome. Examples of such indicators may be found in Cohn et al, *Cancer* 79:233–44 (1997), Finkelstein et al, *Cancer* 71(12):3827–3838 (1993), Harrison et al, *Human Pathology* 26(1):31–38 (1995), Furuta et al, *Clinical Cancer Research* 4:21–29 (1998), Tanigawa et al, *Cancer Research* 57:1043–1046 (1997), Ropponen et al, *Cancer Research* 58:342–347 (1998), Wielenga et al, *Cancer Research* 53:4754–4756 (1993), Halter et al, *Modern Pathology* 5(2):131–134 (1992), Tanabe et al, *Lancet,* 341:725–726 (1993), Lanza et al, *Anatomic Pathology* 105(5):604–612 (1996), Graham et al, *Modern Pathology* 3(3):332–335 (1990), Engel et al, *The American Journal of Surgical Pathology* 20(10):1260–1265 (1996), Suzuki et al, *Gastroenterology* 109:1098–1104 (1995), Morrin et al, *Gut* 35:1627–1631 (1994) and Nakamori et al, *Gastroenterology* 106:353–361 (1994).

Colorectal cancer has variable clinical outcome from being cured by surgery or other treatment to recurring with poor prognosis. The potential to predict inoperable cancer, metastatic tumors or simply tumors which require more aggressive treatment has prompted the search for new prognostic markers that would be applied to the colorectal polyp biopsy. Such indicators should prove successful in selecting therapy and predicting disease outcome after diagnosis and before or at any time during treatment. Since severe patient distress can be caused by more aggressive therapy regimens, it is desirable to determine when such therapies are warranted.

For example, patients with a high likelihood of relapse can be treated aggressively with powerful systemic chemotherapy and/or radiation therapy in addition to surgery. When a lesser likelihood of relapse or rapid death is determined, less aggressive therapies can be chosen. It is also desirable to identify those patients who might be candidates for newly developed target-specific therapies such as those described herein.

Unfortunately, following treatment the cancer frequently recurs and sometimes drug resistance develops, particularly in metastatic disease or when diagnosed earlier in life. This results in the tumors eventually regrowing. In such a situation, the tumors are frequently unresponsive to the previous treatment. Furthermore, many metastatic tumors arise in drug-resistive tissues such as the brain, and do not respond to certain chemotherapeutic agents at all.

There is thus a clear need for new assays to predict which tumors would likely respond to particular treatment regimes such as the aforesaid treatment or alternative therapeutic approaches thereby allowing an attending physician to select the most appropriate course of therapy.

A percentage of people are refractory to therapy at the onset. Most respond initially and if they are going to become resistant, developed symptomatic metastases after months or years of drug-based therapy. It is assumed that either new genetic mutations occur in the "dormant" metastatic sites that confers the ability for the tumor to grow again or that clones of drug-independent tumor that were "masked" by the initially faster growing susceptible cells. The resistant tumor cells are then permitted to grow without competition as these susceptible cells are suppressed by the drug therapy.

It has been hypothesized that the use of aggressive chemotherapy early in disease treatment, i.e. in a neoadjuvant approach prior to surgery, may hasten the development of the aggressive clones. Thus, a marker that could predict the "risk" that such a treatment with existing or future chemotherapeutic resistant tumors would be of significant clinical value.

Accordingly, there is a clear need for adjuvant or alternative therapeutic approaches to colorectal tumors and are therefore not fully responsive to surgery. New cancer-specific therapeutic products are currently being developed expanding the spectrum of potential treatments.

Several groups have reported various associations between HER-2/neu (erbB-2)protein, mRNA and gene amplification in various tumor cells as a means for determining cancer stage and outcome. The HER-2/neu gene encodes a cell surface protein similar to the epidermal growth factor (EGF) receptor protein, used to receive growth signals. Cell differentiation has been shown to be of value in determining the prognosis of certain cancers, but this factor does not always correlate to gene amplification or overexpression of erbB-2 in certain gastrointestinal cancers. Kameda et al, *Cancer Research* 50:8002–9 (1990) and repeated in Tahara, *Cancer Supplement* 75(8):1410–1416 (1995).

Classically, one can determine the prognosis for breast and other hormone-responding related tumors by measuring HER-2/neu amplification and treat the patient with anti-HER-2/neu antibody accordingly. However, in the field of colon cancer a number of researchers have reached divergent and even opposite conclusions regarding levels of protein, mRNA and DNA gene copy numbers of erbB2, also known as HER-2/neu, and also know as p185. For example, Kapitanovic et al, *Gastroenterology* 112(4):1103–1113 (1997) suggests a correlation between protein (measured by Western Blot) and colon cancer prognosis. Hu et al, *Chung Hua Chung Liu Tsa Chih* 18(4):247–249 (1996) states no correlation exists when measuring protein immunohistochemically. Other cancer systems known to have a correlation between erbB-2 and prognosis don't serve as good models for colon cancer as Caduff et al, *Verh. Desch. Ges. Pathol.* 81:219–227 (1997) measured erbB2 immunohistochemically and concluded the molecular mechanisms in endometrial carcinoma (a hormone related cancer) are different from colorectal carcinomas.

Measuring gene amplification (number of copies of the gene) of HER-2/neu (erbB-2) in colon carcinoma has also provided divergent results. Wang et al, *Chung Hua I Hsueh Tsa Chih* 74(9):536–538 (1994), found amplification of the gene (by differential PCR) more often in metastatic colon cancer but the difference was not significant. By comparison Knyazev et al, *Oncology* 49(2):162–165 (1992) and Tal et al, *Cancer Research* 48(6):1517–20 (1988) found only 1 out of 19 and 6 out of 109 colon carcinomas were erbB-2 amplified. Still further Gutman et al, *International Journal of Cancer* 44(5):802–5 (1989), found no association between amplification (measured by Southern Blotting) and a specific stage or prognosis. When measuring mRNA, Yang et al, *Anticancer Research* 17:1023–1026 (1997), noted an increased level appearing to correlate to certain types of metastasis but not others types of metastasis.

The reason for this divergence of results with colon/colorectal cancer is unclear but different groups use an assortment of different research techniques with different "home brews" of reagents on samples processed in a different manner. One difficulty arises when one measures protein expression instead of gene amplification. Another difficulty ocurrs when one measures tissues to determine an average gene copy rather than individual cells which may determine a rare cancerous cell in a mass of normal tissue.

SUMMARY OF THE INVENTION

In one aspect, the invention relates to a method for predicting the outcome of colorectal cancer in a particular patient by determining their HER-2/neu gene amplification status by in-situ hybridization.

In another aspect, the present invention relates to a method for treating colorectal cancer based on by using compositions that block expression of the HER-2/neu oncogene or function of the gene product.

In a related aspect, the invention relates to the combination of conventional anti-colorectal therapy and an inhibitor of HER-2/neu to treat colorectal cancer.

In a related aspect, the invention relates to a method for testing for HER-2/neu gene amplification and treating colorectal cancer using conventional anti-colorectal cancer therapy in patients which do not have the HER-2/neu gene amplified.

In another aspect, the invention relates to a method for selecting treatment for colorectal cancer based on the determination of the number of copies of HER-2/neu gene in colorectal cells from the patient. When the number of copies is abnormally high, aggressive therapy and/or treatment with an inhibitor of HER-2/neu is indicated. In such a situation, watchful waiting or mild treatment in lieu of or post surgery would be contraindicated.

BRIEF DESCRIPTION OF THE DRAWINGS

FIG. 1 is a survival curve for colorectal cancer when the tumor cells are with and without HER-2/neu gene amplification.

DESCRIPTION OF THE PREFERRED EMBODIMENTS

The term "colorectal cancer" includes adenocarcinoma and carcinoma of the colon whether in a primary site or metastasized.

An "anti-colorectal" is an effective chemical, radiation or surgical or other treatment which reduces the amount of functioning colorectal cancer cells. Current "conventional anti-colorectal" chemical therapies include 5-fluorouracil, levamisole, leucovorin and semustine (methyl CCNU). Anti-HER-2/neu compositions are not considered anti-colorectal compositions for the purposes of this definition even though as the result of the present invention, they should be considered so in the future. Effective dosages are well known in the art and is standard oncology practice.

An "anti-HER-2/neu composition" includes compositions which act specifically on the HER-2/neu DNA, the HER-2/neu mRNA (spliced or not), and/or the HER-2/neu protein. (Erb-B2is believed to be the same as HER-2/neu and sometimes is also referred to as p185 in certain situations). The protein, mRNA and DNA may use the same names. Examples of a composition which acts on the DNA and RNA include anti-sense oligonucleotides or triple strand forming oligonucleotides which code for a DNA or RNA complementary to or otherwise capable of binding HER-2/neu mRNA or HER-2/neu DNA, thereby preventing its transcription, splicing or translation into protein. See Noonberg et al, Gene 149: 123–126 (1994). Antisense oligonucleotides may also be used. Ribozymes may also be used which catalytically alter the HER-2/neu gene or mRNA. See Wiechen et al, Cancer Gene Therapy, 5(1)45–51 (1998). Examples of compositions which act on the protein include antibodies, fragments and derivatives thereof, or other protein binding agents to the HER-2/neu protein; peptides which exhibit sufficient homology to the tyrosine kinase growth factor ligand to bind to and inactivate the HER-2/neu protein; antagonizing analogs to the HER-2/neu receptor; small molecule signal transduction inhibitors (Sugen, Inc., Redwood City, Calif.), a vaccine or other immunological preparations containing a chemical moiety resembling the HER-2/neu protein and capable of eliciting an immune response (antibodies or cellular immunity) against the HER-2/neu protein and compositions, such as enzymes, which modify the protein by cleavage, altered glycosylation or altered three dimensional configuration. An example of a composition which counters the action of HER-2/neu is a drug with an anti-growth activity. Preferred compositions are a recombinant humanized monoclonal antibody such as Herceptin™ (Genentech, South San Francisco), MDX-210 (Medarex), a bispecific antibody combination binding with HER-2/neu and DC-64 and having the capability of directly linking the body's immune cells to the target cancer cells and peptide vaccines of Corixa Corp (Disis, ASCO conference, May 1998. A more complete description of Herceptin™ and its use is found is found in Hudziak et al, U.S. Pat. No. 5,725,856. Dosages have been standardized for the treatment of breast cancer and the same ranges may be used for colon cancer as well. Other dosage ranges are given in Hudziak et al. Other antibodies to HER-2/neu may also be used. Alternative treatments may include any therapeutic products designed to attack breast cancer cells expressing elevated levels or gene copy numbers of HER-2/neu. At the present time, somewhat useful chemotherapy has been established for colorectal cancer. Such chemotherapy can also be administered in combination with, subsequent to or prior to conventional anti-colorectal treatments. Enhancing therapy to promote the anti-cancer effects may also be used, such as GM-CSF.

These compositions, which may include for example antibodies, vaccines, and gene therapy approaches, would be preferably employed in those tumors wherein the HER-2/neu gene is amplified. Similar therapeutic approaches have been successfully employed in battling breast cancer. See Drebin et al, *Cell* 42: 695–706 (1985), Drebin et al, *Oncogene* 2: 273–277 (1988), Drebin et al, *Oncogene* 2: 387–394 (1988) and Fendley et al, *Cancer Research* 50:1550–1558 (1990). However, it was heretofore unknown and unexpected that such agents could be used against colorectal tumors. See Baselga et al, *Journal of Clinical Oncology* 14: 737–744 (1996), Cobleigh et al, *Proc. ASCO* 17:97a (1998) and Slamon et al, *Proc. ASCO* 17:98a (1998).

The HER-2/neu protein is a cell membrane tyrosine kinase that is a member of the epidermal growth factor receptor family.

The data in the present invention demonstrates that amplification of HER-2/neu correlates to a decreased chance of long term survival and a shortened time to relapse of the disease. Determination of the HER-2/neu copy number in the colorectal cells from an initial or historical biopsy in accordance with the present invention can be used to identify patients with a biologically aggressive form of colorectal cancer. The expected number of signals in a normal cell and in an unamplified tumor cell varies from 2 to 4 depending on the phase of the cell cycle. A cell with five or more signals is considered amplified. Individuals with cells in which amplification of the HER-2/neu gene is observed require different or more aggressive treatment.

Conversely, patients having colorectal cancer with a low copy number of HER-2/neu can be treated with milder conventional therapy, such as simple surgery, to lessen or avoid adverse side effects while effectively treating the cancer thereby avoiding radiation or drug exposure entirely until such time as some therapeutic intervention is indicated.

The reason why such information is important is that HER-2/neu gene amplification detection by FISH allows for improved risk stratification for patients with low-stage colorectal cancer. For patients with $T^1$ (Dukes A) and $T^2$ (Dukes $B^1$) tumors, adjuvant chemotherapy is not currently recommended. When these early stage tumors feature HER-2/neu gene amplification, their recurrence/metastasis risk is significantly higher than unamplified tumors and should be considered for adjuvant therapy. HER-2/neu positive tumors that relapse should be considered for anti-HER-2/neu therapy such as HERCEPTIN®.

In addition to traditional treatments such as surgical intervention, and higher doses of radiation, alternative methods of treatment for colorectal and other cancers are being developed. Alternative treatments may include therapeutic products designed to attack specific cancer cells. Specifically, compositions directed against cancers which exhibit overexpression of the HER-2/neu protein would be desirable. Such compositions include antibodies, or fragments thereof, to the HER-2/neu protein and peptides which exhibit sufficient homology to the tyrosine kinase growth factor ligand. These compositions may be linked to a marker moiety, which is readily recognized as foreign by the patient, and cytotoxic moieties (e.g. ricin chain) or structures (liposomes, etc. containing a drug).

Unfortunately, some colorectal carcinomas eventually recur with difficult to treat tumors. The HER-2/neu gene amplification rate for people with recurrent disease was about 80%, whereas the amplification rate for people with non-recurrent colorectal cancers is 20% according to the inventor's data.

While advanced colorectal cancers are typically the most demanding in treatment effectiveness, the treatments of the present invention may also be used for early stage colorectal cancers which are HER-2/neu amplified indicating aggressiveness. Since treatment of localized tumors is generally more successful than when the patient has advanced cancer, early treatment, even at the point of initial diagnosis is within the present invention.

Anti-HER-2/neu and conventional chemotherapeutic compositions used are pharmaceuticals (biologicals, e.g. vaccines, are considered pharmaceuticals) and typically are mixed with a vehicle or carrier and which are pharmaceutically acceptable. The nature of the pharmaceutically acceptable carrier or vehicle, its selection and formulation based on active ingredient and route of administration is well known to those skilled in the art.

When two compositions are used, they may be mixed in the same container, unitary dosage or they be in separate containers. In either situation, a kit may be formed containing one or more of the compositions along with instructions for usage treating colorectal cancer. The kit may be in a number of different configurations such as one or more containers in a single box or other manner linking the two compositions in close proximity to each other. Also, the linkage may be indirect by way of the instructions contained in packages of one or both drugs.

To detect HER-2/neu overexpression, one may assay for an excess amount of the HER-2/neu protein by immunoassay using, for example, reagents supplied by Ventana Medical Systems, Inc (Tucson, Ariz.) or other diagnostic protein assay such as gel electrophoresis. It is also within the scope of the present invention to detect overexpression of HER-2/neu by measuring HER-2/neu mRNA. As the HER-2/neu gene tends to be amplified by repeating an amplicon, the determination of other amplified genes, located nearby in the genome and in the same amplicon, would be a suitable proxy for actual HER-2/neu gene amplification detection. Thus, the present invention includes detecting other coamplified genes or DNA in the amplicon.

The reported data relating to a different cancer, namely prostate cancer and HER-2/neu has been extremely variable with a number of "negative" studies concerning prognostic significance. However, when gene amplification was measured using in-situ hybridization using a FDA approved test, an accurate prognostic indicator for prostate cancer was obtained. Similar unpredictable results have been noted in colorectal cancer as noted above. Accordingly, the present invention measured HER2/neu gene amplification by in-situ hybridization, particularly highly standardized versions, e.g. the FDA approved version.

In the present invention, the number of copies of the HER2/neu gene are detected. This may be done by a number of techniques, perhaps the easiest and apparently the most accurate of which is by in-situ hybridization. Normal cells contain 2 copies of each gene. After DNA replication and just before cell division, a cell may have 4 copies of a gene. The detection of five or more copies of the HER-2/neu gene in a single cell clearly indicates the presence of amplified HER-2/neu genes. In a sample, one would expect many normal unamplified cells. In situ hybridization assays have the ability to find a minority of cells which are abnormal.

Fluorescence in-situ hybridization (FISH) and other gene detection methods may be used in accordance with the present invention to detect amplification of HER-2/neu genes in colorectal tissue and provide a reliable technique for identifying suitable candidates for anti-HER-2/neu treatment. Identification of an amplified HER-2/neu status is preferably performed early in the diagnostic process, such as at the biopsy stage. Prompt treatment with anti-HER-2/neu treatment may be used to prevent the progression of the disease to more advanced stages or effect remissions. Additionally, patients who have certain forms of the disease may derive a clinical benefit from the administration of an anti-HER/2-neu treatment in combination with conventional anti-colorectal cancer treatments.

In accordance with the present invention increased copy number of the HER-2/neu gene in colorectal tissues is detected using FISH techniques (INFORM®, Ventana Medical Systems Inc., Gaithersburg, Md., the contents and methodology of which is incorporated by reference). A brief overview of the in-situ hybridization assay follows. The structure of the HER-2/neu gene is well known. See, e.g., King et al., Science, 229:974–978 (1985) and Coussens et al., Science, 230:1132–1139 (1986). Detectable DNA probes capable of hybridizing to the known HER-2/neu gene sequence are constructed and labeled using conventional techniques. See, for example, PCT Application Pub. No. WO94/09022, the entire contents of which are incorporated herein by reference. Examples of labeling systems include those which incorporate digoxygenin, biotin, avidin, streptavidin and antibodies. Labeled DNA probes are then allowed to hybridize to available HER-2/neu genes and are detected using conventional fluorescence detecting techniques such as fluorescence microscopy, spectrophotometers, fluorescent plate readers and flow sorters. For signal detection, fluorescent molecules can be linked directly to the DNA probe or can be linked to a binding partner for the probe. Useful fluorescent molecules include, but are not limited to fluorescein, amino coumarin acetic acid, tetramethylrhodamine isothiocyanate, Texas Red, Cy3.0, Cy5.0, and green fluorescent protein. Other non-fluorescent labels may be used such as chemiluminescent, radioactive, enzyme, ligand, spin labels, quenchers etc., and the choice is well known and within the skill of the art. The selection among known labels in the DNA hybridization and other binding assays (e.g. immunoassay). Signal detection and amplification techniques known to those skilled in the art can be utilized in accordance with the present invention. Thus, signal detection and amplification techniques such as those involving streptavidin/biotin, avidin/biotin, hapten conjugates such as digoxygenin/anti-digoxygenin, dinitrophenyl/anti-DNP and other known antibody based detection and amplification techniques are utilized herein.

The following examples are included for purposes of illustrating certain aspects of the invention and should not be construed as limiting.

EXAMPLE 1

Samples and Assays

Archival formalin-fixed, paraffin-embedded tissue sections from 99 patients with colorectal adenocarcinoma were immunostained for MIB1 cell proliferation marker (Ventana Medical Systems, Tuscon, Ariz.) and p34$^{cdc2}$ cyclin dependent kinase (Biogenex, San Ramon, Calif.) by automated methods (Ventana) . HER2/neu gene amplification was determined by FISH according to the methods of Example 2 below. All methods were compared to patient survival.

EXAMPLE 2

Fish Assay for Her-2/neu

Samples of colorectal adenocarcinoma tissue sections were deparaffinized and an assay was performed by a HER-2/neu unique sequence probe or the Inform® HER-2/neu Gene Detection System (FDA approved version). Briefly, unstained four micron formalin-fixed paraffin-embedded tissue sections were applied to silanized slides and processed according to the Oncor chromosome in-situ hybridization system (Oncor, Inc., Gaithersburg, Md.). Tissue deparaffinization in xylene was followed by transfer through two changes of 100% ethanol and the slides were allowed to air dry. The slides were then immersed for 30 minutes in 30% Oncor pretreatment solution (30% sodium bisulfite in 2×SSC (0.45 molar NaCl and 0.045 molar sodium citrate)) at 45° C. and 45 minutes in Oncor protein digesting solution (0.25 mg/ml proteinase K in 2×SSC) at 45° C. After a brief wash in 2×sodium chloride/sodium citrate (SSC) slides were dehydrated in 100% ethanol and allowed to air dry.

Oncor unique sequence digoxygenin-labeled HER-2/neu DNA probe consisting of 4 contiguous overlapping cosmid probes which create a 90 kb unbroken DNA strand (Oncor, Inc. Catalog Nos. P5111-BIO, P5111-DIG, P5111-B.5, P5111-DG.5, S8000-KIT or S8000-KIT-E) was prewarmed for five minutes at 37° C. prior to application. The amount of probe hybridization mixture was approximated according to the target area and the size of the coverslip to be placed over the tissue during hybridization (10 μl probe mixture per 22×22 mm coverslip area). Denaturation was accomplished at 69° C. for five minutes and the slides were then incubated overnight at 37° C. in a pre-warmed humidified chamber. Following overnight hybridization, the slides were again immersed in 2×SSC and pre-warmed to 72° C. for a five minute stringency wash in 40 ml 2×SSC at pH 7.0 prior to detection. Fluorescein-labeled anti-digoxygenin (commercially available from Boerhinger Mannheim) in a solution containing 5% nonfat dry bovine milk, 0.08% sodium azide, 0.05% NP-40, 0.1 molar $NaH_2PO_4$ and 0.1 molar $K_2HPO_4$ was applied and a plastic coverslip placed gently for a 20 minute incubation at 37° C. in a pre-warmed humidified chamber in the dark. After careful removal of the coverslip and rinsing of excess detection compounds in 1×phosphate-buffered detergent (PBD) for three rinses at two minutes each, slides were counterstained with 18 μl of propidium iodide/antifade (1:4) and covered with a glass coverslip. Slides were evaluated for HER-2/neu gene copy number using a Zeiss Axioskop 50 fluorescence microscope.

The probe displays a single fluorescent signal at the location of each copy of the HER-2/neu gene. The expected number of signals in a normal cell and in an unamplified tumor cell varies from 2–4 depending on the phase of the cell cycle. A cell with five or more signals was considered amplified. A minimum of 100 tumor cells in each colorectal carcinoma specimen was evaluated for the number of nuclear HER-2/neu signals. Amplified tumors were defined as having a minimum of 20 cells with five signals or greater per cell. The number of signals was not averaged between cells.

EXAMPLE 3

Independent Results of Her-2/neu Gene Copy Number 15 of 99 cases (15%) showed amplification of the HER-2/neu gene. 90 of 99 cases showed positive immunostaining for p34$^{cdc2}$. 12 of 15 cases (80%) with HER-2/neu gene amplified died. 29 of 84 cases (35%) with HER-2/neu gene unamplified died. On univariant analysis, pathologic stage (p<0.001) and HER-2/neu (p<0.003) correlated with length of survival. When cases were stratified by cell proliferation index (CPI), those with high proliferation or CPI>20 (7%) showed a trend toward correlation with survival (p=0.078).

Positive immunostaining for $p34^{cdc2}$ did not correlate with survival. On multivariate analysis, clinical stage (p<0.001) and HER-2/neu gene amplification (p=0.028) independently predicted survival. The survival curve for colorectal cancer with both HER-2/neu amplified and unamplified tumors is shown in FIG. 1.

EXAMPLE 4

HER-2/neu Copy Number and Patient Therapy Response to Recombinant Humanized Monoclonal Antibody to HER-2/neu To evaluate the effectiveness of recombinant humanized monoclonal antibody to HER-2/neu treatment in 23 colorectal cancer patients with advanced stage disease due to recurrence after surgery, and no history of other malignancy, except non-melanoma skin cancer, the following study is performed.

To participate in the study, patients must demonstrate progression of colorectal adenocarcinoma after surgery and at least one other treatment, either radiation or chemotherapy. Progressive disease is defined by evidence of new lesions by X-ray, MRI or surgical removal. Alternatively, evidence of a greater than 25% increase in tumor size constitutes progression. Additionally, to rule out patients experiencing an improvement due to chemotherapy withdrawal or following surgery or radiation, some of the patients in the study are required to show progression of the disease and be off of other therapy for at least four weeks prior to enrollment.

Fresh or archival biopsy or surgically removed tumor cells are assayed for HER-2/neu amplification using the technique of Example 2.

Patients receive 4 mg/kg Herceptin™ (Genentech, Inc., South San Francisco, Calif.) administered IV over 90 minutes, as a loading dose on Day 0. Subsequently, 2 mg/kg is administered IV over 30 minutes weekly for up to 24 weeks, or until disease progression or unacceptable side effects necessitated removal of the patient from the study.

The results of this study indicate whether treatment with Herceptin™ bestows a clinical benefit by slowing or halting the progression of the colorectal cancer. Additionally, administration of Herceptin™ as a single agent confers a survival advantage in colorectal cancer patients whose colorectal cells from the initial biopsy demonstrated HER-2/neu amplification as compared to patients without HER-2/neu amplification.

Early intervention by identifying the colorectal cancer patient at the time of the initial biopsy as being HER-2/neu amplified and beginning Herceptin™ treatment is expected to enhance the patients chances of survival by slowing or stopping progression of the disease while avoiding treatment in individuals who are not expected to significantly benefit from Herceptin™ treatment.

EXAMPLE 5

Treatment of Colorectal Cancer with a HER-2/neu Vaccine with Optional Chemotherapy Treatment The techniques of Example 4 are repeated on another group of 17 colorectal cancer patients fulfilling the same criteria. However instead of receiving Herceptin™ treatment, the patients are vaccinated with a HER-2/neu vaccine (MDX-210, Medarex) previously proposed for treating breast cancer.

The response is quantified using the criteria in EXAMPLE 5. While not actually used in this Example for technical reasons, the formation of anti-HER-2/neu antibody and/or cellular immune response in the patient's serum may be measured, correlated to all other medical data and used as a predictor of prognosis or determination of further treatment also.

The results of this study indicate whether the vaccine alone or combined with conventional chemotherapy bestows a clinical benefit by slowing or halting the progression of the colorectal cancer.

The effectiveness of this treatment indicates that earlier treatment of colorectal cancer at the time of the initial biopsy, indicating HER-2/neu amplified, with a vaccine to HER-2/neu alone or combined with other treatment is expected to enhance the patients chances of survival by slowing or stopping progression of the disease.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

All patents and references cited herein are explicitly incorporated by reference in their entirety.

What is claimed is:

1. A method for treating colorectal cancer comprising:
   administering to a patient in need of such treatment a therapeutically effective amount of an anti-HER-2/neu composition.

2. The method of claim 1 wherein said anti-HER-2/neu composition comprises an antibody or fragment thereof.

3. The method of claim 2 wherein said anti-HER-2/neu antibody is a recombinant humanized monoclonal antibody.

4. The method of claim 1 wherein said anti-HER-2/neu composition comprises a peptide or protein.

5. The method of claim 1 wherein cells from the patient have a HER-2/neu gene copy number exceeding 4 copies per cell.

6. The method of claim 1 wherein said anti-HER-2/neu composition comprises an oligonucleotide.

7. The method of claim 1 wherein the colorectal cancer has recurred after surgical removal or other therapy.

8. The method of claim 4 wherein the protein or peptide is a vaccine.

* * * * *